(12) United States Patent
Guerrini et al.

(10) Patent No.: US 11,167,084 B2
(45) Date of Patent: Nov. 9, 2021

(54) CONTROL DEVICE FOR CONTROLLING THE ADMINISTRATION OF PROPOFOL TO A PATIENT

(71) Applicant: Fresenius Vial SAS, Brézins (FR)

(72) Inventors: Alexandre Guerrini, Fontaine (FR); Pauline Cottin, Voiron (FR)

(73) Assignee: Fresenius Vial SAS, Brézins (FR)

( * ) Notice: Subject to any disclaimer, the term of this patent is extended or adjusted under 35 U.S.C. 154(b) by 20 days.

(21) Appl. No.: 16/098,086

(22) PCT Filed: Apr. 21, 2017

(86) PCT No.: PCT/EP2017/059502
§ 371 (c)(1),
(2) Date: Oct. 31, 2018

(87) PCT Pub. No.: WO2017/190966
PCT Pub. Date: Nov. 9, 2017

(65) Prior Publication Data
US 2019/0143040 A1    May 16, 2019

(30) Foreign Application Priority Data

May 2, 2016 (EP) .................................... 16305507

(51) Int. Cl.
*A61M 5/172* (2006.01)
*A61B 5/00* (2006.01)
(Continued)

(52) U.S. Cl.
CPC ......... *A61M 5/1723* (2013.01); *A61B 5/4821* (2013.01); *A61K 31/05* (2013.01);
(Continued)

(58) Field of Classification Search
CPC .. A61M 2202/048; A61M 2005/14296; A61M 19/00; A61B 5/4821
See application file for complete search history.

(56) References Cited

U.S. PATENT DOCUMENTS 7,220,240 B2    5/2007    Struys et al.
9,649,063 B2    5/2017    Kokko
(Continued)

FOREIGN PATENT DOCUMENTS

CN    101046831 A    10/2007
CN    201049111 Y    4/2008
(Continued)

OTHER PUBLICATIONS

Absolom et al., "Pharmacokinetic models for propofol-defining and illuminating the devil in the detail", British Journal of Anesthesia, 2009, pp. 26-37, vol. 103, No. 1.
(Continued)

*Primary Examiner* — Emily L Schmidt
(74) *Attorney, Agent, or Firm* — Cook Alex Ltd.

(57) ABSTRACT

The invention relates to a control device for controlling the administration of propofol to a patient according to the preamble of claim 1 and to a method for controlling the administration of propofol to a patient according to the preamble of claim 4. With a method of this kind a bispectral index (BIS) target value is set which shall be, at least approximately, reached within a patient. A controller then computes a recommended infusion rate of propofol based on the target BIS value and further based on a measured propofol level of the patient for administering propofol to the patient. The controller herein comprises a model unit for computing the recommended infusion rate such that, using the model unit for determining the propofol sensitivity of a patient by means of a mathematical model taking into account the bispectral index (BIS) value and optionally the
(Continued)

measured propofol level as input variables, the recommended infusion rate for administering propofol to the patient to achieve the BIS target value may be determined.

19 Claims, 5 Drawing Sheets

(51) Int. Cl.
| | | |
|---|---|---|
| *A61M 5/168* | (2006.01) | |
| *G16H 20/17* | (2018.01) | |
| *G16H 50/30* | (2018.01) | |
| *G16H 40/63* | (2018.01) | |
| *A61K 31/05* | (2006.01) | |
| *A61M 5/142* | (2006.01) | |

(52) U.S. Cl.
CPC ........ *A61M 5/16877* (2013.01); *G16H 20/17* (2018.01); *G16H 40/63* (2018.01); *G16H 50/30* (2018.01); *A61M 2005/14296* (2013.01); *A61M 2202/048* (2013.01); *A61M 2205/50* (2013.01); *A61M 2205/502* (2013.01); *A61M 2205/70* (2013.01); *A61M 2230/20* (2013.01)

(56) References Cited

U.S. PATENT DOCUMENTS

| | | | |
|---|---|---|---|
| 2003/0036744 A1* | 2/2003 | Struys | A61M 5/172 604/503 |
| 2003/0176804 A1 | 9/2003 | Melker | |
| 2004/0079372 A1 | 4/2004 | John et al. | |
| 2006/0009733 A1 | 1/2006 | Martin | |
| 2010/0094202 A1 | 4/2010 | Edginton et al. | |
| 2015/0038940 A1 | 2/2015 | Kreuer et al. | |
| 2015/0164412 A1 | 6/2015 | Kokko | |
| 2016/0089494 A1 | 3/2016 | Guerrini | |
| 2016/0103977 A1 | 4/2016 | Mandel | |
| 2018/0296759 A1* | 10/2018 | Dumont | A61B 5/4821 |

FOREIGN PATENT DOCUMENTS

| | | |
|---|---|---|
| CN | 103163218 A | 6/2013 |
| CN | 103212119 A | 7/2013 |
| CN | 104302342 A | 1/2015 |
| EP | 1832993 A1 | 9/2007 |
| JP | 2003531691 A | 10/2003 |
| JP | 4889177 B2 | 3/2012 |
| JP | 2015512698 A | 4/2015 |
| WO | 0183007 A2 | 11/2001 |
| WO | WO2004/112603 A1 | 12/2004 |
| WO | WO2008/086624 A1 | 7/2008 |
| WO | WO2009/050736 A1 | 4/2009 |
| WO | WO2012/024106 A2 | 2/2012 |
| WO | 2013135240 A1 | 9/2013 |
| WO | WO2014/173558 A1 | 10/2014 |
| WO | WO2015/067956 A1 | 5/2015 |

OTHER PUBLICATIONS

Iannuzzi et al., "Relationship between bispectral index, electroencephalographic state entropy and effect-site EC50 for propofol at different clinical endpoints", British Journal of Anesthesia, 2005, pp. 613-616, vol. 94.

Irwin et al., "Propofol effective concentration 50 and its relationship to bispectral index", Anesthesia, 2002, pp. 242-248, vol. 57.

Lim, "Relationship between bispectral index and effect-site EC for propofol", British Journal of Anesthesia, 2006, pp. 267-268.

Marsh et al., "Pharmacokinetic model driven infusion of propofol in children", British Journal of Anesthesia, 1991, pp. 41-48, vol. 67.

Schnider et al., The influence of method of administration and covariates on the pharmacokinetics of propofol in adult volunteers, Anesthesiology, 1998, pp. 1170-1182, vol. 88, No. 5.

White, et al., "Intravenous propofol anaesthesia using a computerized infusion system", Anesthesia, 1990, pp. 204-209, vol. 45.

International Search Report and Written Opinion for International Application No. PCT/EP2017/059502 dated Jul. 17, 2017.

* cited by examiner

CONTROL DEVICE FOR CONTROLLING THE ADMINISTRATION OF PROPOFOL TO A PATIENT

CROSS-REFERENCE TO RELATED APPLICATIONS

The present application is a U.S. national phase application of International Patent Application No. PCT/EP2017/059502, filed Apr. 21, 2017, which claims the benefit of and priority to EP16305507.2, filed May 2, 2016, both of which are incorporated by reference herein in their entireties.

The invention relates to a control device for controlling the administration of propofol to a patient according to the preamble of claim 1 and to a method for controlling the administration of propofol to a patient according to the preamble of claim 4.

With a method of this kind a bispectral index (BIS) target value is set which shall be, at least approximately, reached within a patient. A controller then computes a recommended infusion rate of propofol based on the target BIS value and optionally further based on a measured propofol level of the patient for administering propofol to the patient. The controller herein comprises a model unit for computing the recommended infusion rate such that, using the model unit for determining the propofol sensitivity of a patient by means of a mathematical model taking into account the bispectral index (BIS) value and optionally the measured propofol level as input variables, the recommended infusion rate for administering propofol to the patient to achieve the BIS target value may be determined.

A method of this kind and a corresponding control device for carrying out such a method may in particular be used to provide a personalized, patient specific anesthesia in a patient. In terms of medical needs, said method and said corresponding control device for carrying out such a method aim to reduce over- or under-infusion of anesthetic drugs and prevent potential side effects. Said method and said corresponding control device are further suitable to take real-time metabolism of the patient into account. The controller used in said method and corresponding control device allows avoiding of overdosing, in particular when a system with high delay is used for administering the anesthetic, such as propofol, to a patient.

In recent years propofol has emerged as the most suitable and as a widely used intravenous anesthetic. Propofol offers many advantages as a total intravenous anesthetic in terms of its pharmacokinetic profile, but anesthetists still have difficulties with the use of intravenous agents to maintain anesthesia compared with standard volatile anesthetics delivered via calibrated vaporizers. Various suggestions have been made for suitable infusion rates of propofol to maintain satisfactory anesthesia. Besides manual infusion schemes, computer-controlled infusion of propofol designed to achieve a constant blood level throughout the duration of surgery has been proposed. However, such a scheme has the principal disadvantage of inability to vary the blood propofol concentration in response to changing surgical and anesthetic requirements. Volatile agents may then have to be introduced to maintain adequate anesthesia.

The pharmacokinetics of propofol is affected by several factors. In the publication Thomas W. Schnider et al., "The influence of method of administration and covariates on the pharmacokinetics of propofol in adult volunteers", *Anesthesiology*, 1998, 88(5) pages 1170-82, it was demonstrated that the method of administration (bolus vs. infusion), influences the pharmacokinetics of propofol.

In the publication M. White and G. N. C. Kenny; "Intravenous propofol anaesthesia using a computerized infusion system", *Anaesthesia*, 1990, Volume 45, pages 204-209, a computer-controlled device for the infusion of propofol has been constructed, which allows the variation of the blood propofol concentration in response to changing surgical and anesthetic requirements. The performance of this system has been evaluated by comparing the predicted blood concentrations of propofol selected by the anesthetist to produce a satisfactory level of anesthesia with the values measured from blood samples. This system has, however, the disadvantage that it is not possible to measure intravenous anesthetic blood concentrations in real time.

In the meantime, a pharmacokinetic-based computer-controlled infusion systems, as for example the Diprifusor system (AstraZeneca Pharmaceuticals, UK) have become commercially available, which have been developed to achieve and maintain target blood concentrations of propofol with a reasonable degree of accuracy.

"Target Controlled Infusion" (TCI) refers to a computer-assisted infusion system which calculates a substance concentration in a particular body tissue on the basis of mathematical models and which, after setting a target concentration by the anesthetist, adjusts the infusion rate until the target concentration is reached. TCI infusion systems consist of an infusion system (syringe pump system) and a computer or microprocessor. Via a monitor or human machine interface, parameters such as patient age, weight, gender, type of anesthetic and the desired pharmacokinetic model as well as the target concentration of the substance to be administered into the patient's blood, can be defined. The microprocessor calculates the infusion rates and controls the syringe pump and the monitor based on these data. Audible and visual signals inform the anesthetist about infusion problems (such as disconnection, closing, end of infusion, etc.). In addition, the monitor displays both, graphically and numerically, the current infusion history, the infused volume and the expected concentration-time curve at the stop of the infusion. In principle, all short-acting intravenous anesthetics with known pharmacokinetics and pharmacodynamics are suitable for TCI control.

On the basis of an empirically determined population-pharmacokinetic model and using a known pharmacokinetic and patient-specific pharmacodynamic parameter set of a medicament (for example, propofol) as well as by means of patient-specific data, a TCI pump calculates a concentration over time in the patient's plasma or at the effect site (brain). Interactions with additionally used anesthetics also require a dose adjustment of propofol. A major problem in controlling the anesthesia supply via TCI systems is selecting the correct individual target value for the appropriate depth of anesthesia, as the patient-specific pharmacokinetics and pharmacodynamics may differ from the underlying population pharmacokinetic model. The accuracy of the concentration calculation also depends crucially on the choice of the mathematical model. Many TCI systems use the mathematical models for propofol application developed by Marsh et al and Schnider et al. The evaluation of the Marsh model for propofol revealed a deviation between −7% and +30%, in one case by 84% between the calculated and the real measured propofol in blood. Thus, using a pharmacokinetic model that takes into account more custom variables and which promises a more accurate calculation of the substance concentration, and thus a patient-adapted anesthesia, is desired.

With the development and increasing use of these target-controlled infusion (TCI) systems, a number of research groups have investigated the correlation of propofol concentrations with dynamic effects.

A. R. Absolom et al., Pharmacokinetic models for propofol—defining and illuminating the devil in the detail, *British Journal of Anaesthesia*, 2009, 103 (1), pages 26-37, have discussed pharmacokinetic models for propofol. Early target controlled infusion (TCI) systems were designed to achieve a user-defined plasma target concentration. It became apparent that there was hysteresis in the relationship between plasma concentration and clinical effect, caused by the temporal delay in equilibration between plasma concentrations and the concentration at the sites of action within the central nervous system, referred to as the effect-site. The rate of plasma/effect-site equilibration depends on factors that determine the rate of drug delivery to the effect-site (such as cardiac output and cerebral blood flow) and pharmacological properties that determine the rate of drug transfer across the blood-brain barrier (lipid solubility, degree of ionization, etc). The time course of plasma/effect-site equilibration can be mathematically described by a first-order rate constant typically referred to as the $k_{e0}$. This term is used to describe the rate of removal of drug from the effect-site out of the body, but the effect-site is regarded as having negligible volume, so that there is no need for separate constants describing the rate constants for movement into and out of the effect compartment (the $k_{e0}$ defines the proportional change in each unit of time of the concentration gradient between the plasma and effect-site). With effect-site targeting, the TCI system manipulates the plasma concentration to achieve the effect-site concentration as rapidly as possible. When the effect-site target concentration is increased, the TCI system briefly increases the plasma concentration to an optimal level above the target effect-site concentration. If the target effect-site concentration is reduced the system stops the infusion, allowing the plasma concentrations to fall, thereby generating a concentration gradient out of the effect-site, until the estimated effect-site concentration has fallen to the new target. With effect-site targeting, the magnitude of the plasma concentration overshoot estimated by the system depends critically on the $k_{e0}$ and also on the estimated rate of decline in the plasma concentration. The estimated rate of decline of the plasma concentration also has an influence on the overshoot. Naturally, the net rate of decline caused by re-distribution depends on the concentration gradients between compartments.

Since the accuracy of the estimated plasma concentration itself and the degree of overshoot required depend on the accuracy of several parameters and assumptions, there are multiple potential sources of error. Model errors resulting in excessively high plasma concentrations may well be tolerated by young fit patients, but in frail, elderly subjects, they may result in significant cardiovascular instability.

M. G. Irwin et al. investigated in the publication "Propofol effective concentration 50 and its relationship to bispectral index", *Anaesthesia*, 2002, volume 57, pages 242-8, how a commercially-available TCI system will produce anesthesia in clinical practice and how standard end-points determining anesthesia and loss of consciousness relate to the bispectral index (BIS) and predicted blood and effect site concentrations of propofol. Indeed, as M. G. Irwin and al. demonstrated in their publication, there is a relationship between the propofol effective concentration 50 ($EC_{50}$) and the bispectral index (BIS). This was later confirmed in the publication of M. Iannuzzi et al. "Relationship between bispectral index, electroencephalographic state entropy and effect-site $EC_{50}$ for propofol at different clinical endpoints", *Br J Anaesth*, 2005, 94, pages 613-16, wherein propofol site effect concentrations and BIS were recorded at loss of verbal contact (LVC) and loss of consciousness (LOC).

Additional recent studies have provided results, which were achieved with different patient populations and which confirm the results by Irwin et al. and Iannuzzi et al. These results are summarized in the publication from T. A. Lim "Relationship between bispectral index and effect-site $EC_{50}$ for propofol" *Br J Anaesth*, 2006, 267-268.

With the information now available in the prior art, it is possible to correlate the effect-site concentration and the bispectral index (BIS) of propofol at defined points, e.g. at loss of consciousness (LOC) or at the point of anesthesia, i.e. it is no longer necessary to correlate the effect-site concentration of propofol with nerve response.

However, the published pharmacokinetic models are based on small numbers of patients included in the studies and are not suitable to take real-time metabolism into account.

There is a desire for a safe method for controlling the administration of propofol to a patient which allows in a fast, reliable manner to maintain a patient's propofol level at or around a desired target value, in particular to reduce the risk for under- or overdosing of the anesthetic to the patient.

It is an object of the instant invention to provide a control device and a method for controlling the administration of propofol to a patient which in a reliable, computationally efficient manner allows for maintaining a patient's propofol level at or around a desired target propofol level.

This object is achieved with a control device comprising the features of claim 1 and a method comprising the features of claim 4.

Accordingly,
- a propofol sensitivity of the patient is determined by means of a mathematical model taking into account the bispectral index (BIS) and optionally the measured propofol level in the blood, and
- based on a predefined BIS target value and if available the measured propofol level, a recommended infusion rate for administering propofol to the patient is computed by a controller.

Advantageously, the controller, when computing the recommended infusion rate based on the BIS target value, in addition takes also a measured propofol level of the patient into account. The measured propofol level of the patient herein may be taken into account directly as a parameter when computing the recommended infusion rate or the measured propofol level may be taken into account indirectly via the mathematical model when determining the propofol sensitivity. The propofol sensitivity hence is determined using a mathematical model taking into account, as parameters, the bispectral index (BIS) and if available the measured propofol level in the blood of the patient.

Accordingly, the control device of the invention comprises a depth-of-anesthesia monitor, preferably a bispectral index (BIS) monitor, and optionally a drug sensor for measuring the propofol level.

The instant invention is based on the idea to use a mathematical model to determine a value for the specific, situation-dependent propofol sensitivity of a patient. The model takes into account the bispectral index (BIS) and optionally the actually measured propofol level within a patient. Further, for example the administration of other substances, such as analgesics like Alfentanil® or Remifentanil® is taken into account. The model sets the actual infusion rate and the bispectral index (BIS) into relation with each other, wherein the relation is, among others, quantified by/through the propofol sensitivity.

The bispectral index (BIS) refers to a dimensionless number between 0 (deep anesthesia) and 100 (awake). Publications prove that the BIS closely correlates with various sedation scores and the blood concentration of anesthetics. Typical BIS scores and correlating anesthesia states are as follows:

| BIS | Anesthesia status |
| --- | --- |
| 90-100 | awake |
| 65-85 | Sedation |
| 45-60 | Sufficiently deep anesthesia during general anesthesia |
| 45-35 | Deep narcosis, lack of unconscious memory |
| <40 | Incipient burst suppression |
| <30 | Increasing burst suppression |
| 0 | Baseline EEG |

The model preferably is a so called pharmacokinetic-pharmacodynamic (PK/PD) model taking into account patient-specific parameters such as the patient's height, weight, age, gender, body mass index (BMI) and/or other parameters to model the pharmacodynamics and pharmacokinetics of propofol in the patient.

A PK/PD model for propofol is known in the art as the so-called "3+1 PK/PD model" as described in FIG. 2 below. This model is based on the so called Schnider model or the so called Marsh model.

It has surprisingly be found by the inventors that the reliability of a control device or a method for controlling the administration of propofol to a patient can be improved, when the existing "3+1 PK/PD model" is extended by two further compartments, a remote compartment X and a BIS sensor S. The X compartment is a remote compartment that models the delay of the propofol concentration effect on the bispectral index (BIS). In particular, the physiological delay but also the computational delay potentially induced by the signal processing in the BIS is modeled in the X compartment. The S compartment represents the BIS sensor itself. The inventive model is described in detail in FIG. 3 below.

The extended 3+1 PK/PD model of the invention has several advantages. The inventive model estimates the sensitivity of a patient to propofol and tunes model parameters according to the depth of anesthesia and drug level measurements, if available. In a further embodiment, an adaptive control method is used in the extended 3+1 PK/PD model of the invention. The adaptive control method of the invention has been designed to target a BIS level rather than a target propofol concentration. This invention is particularly suitable for use in operating and intensive care units.

Suitably, the extended 3+1 PK/PD model according to the invention is based on a central compartment A comprising a blood concentration $C_p$ of propofol, a rapid equilibrating compartment $C_{RD}$, a slow equilibrating compartment $C_{SD}$, and an effect compartment E comprising an effect compartment concentration $C_e$ of propofol. The compartments of the extended 3+1 PK/PD model can be calculated as set out in equations 1 to 10:

The S compartment can be calculated according to equation 1:

$$\dot{S} = \frac{s_P X}{\alpha_M + X} - k_{b0}S + OF \quad \text{(Equation 1)}$$

wherein
$s_P$ represents the propofol-sensitivity of the patient;
$\alpha_M$ represents the saturation parameter of the velocity of effect of an anesthetic, such as propofol (i.e. the saturation of the propofol receptors);
$k_{b0}$ represents the decay rate of the BIS index;
OF represents the offset that can remain when no more anesthetic, such as propofol, is present in the patient body;
X represents a remote compartment; and
S represents a BIS sensor.

The X compartment can be calculated according to equation 2:

$$\dot{X} = s_2 C_e - s_1 X \quad \text{(Equation 2)}.$$

wherein
$s_1$ and $s_2$ represent constant transfer rate parameters between the remote compartment and the effect parameters;
$C_e$ represents the effect compartment concentration; and
X represents a remote compartment.

The rapid equilibrating compartment $C_{RD}$ can be calculated according to equation 3:

$$\dot{C}_{RD} = -k_{21} C_{RD} + k_{12} C_p \quad \text{(Equation 3)}$$

wherein
$k_{12}$ is an elimination constant describing the distribution of propofol from the central compartment A in direction of rapid equilibrating compartment $C_{RD}$,
$k_{21}$ is an elimination constant describing the distribution of propofol from rapid equilibrating compartment $C_{RD}$ in direction of central compartment A,
$C_{RD}$ represents the rapid equilibrating compartment, and
$C_p$ represents the blood concentration.

The slow equilibrating compartment $C_{SD}$ can be calculated according to equation 4:

$$\dot{C}_{SD} = -k_{31} C_{SD} + k_{13} C_p \quad \text{(Equation 4)}$$

wherein
$k_{13}$ is an elimination constant describing the distribution of propofol from central compartment A in direction of slow equilibrating compartment $C_{SD}$,
$k_{31}$ is an elimination constant describing the distribution of propofol from slow equilibrating compartment $C_{SD}$ in direction of central compartment A,
$C_{SD}$ represents the slow equilibrating compartment; and
$C_p$ represents the blood concentration.

The effect compartment concentration of propofol $C_e$ can be calculated according to equation 5:

$$\dot{C}_e = -k_{e0} C_e + k_{1e} C_p \quad \text{(Equation 5)}$$

wherein
$k_{e0}$ defines the decay rate for the propofol effect;
$k_{1e}$ describes a "virtual" constant rate transfer from central compartment A and the effect compartment E; and
$C_e$ represents the effect comportment concentration.

The blood concentration $C_p$ of propofol can be calculated according to equation 6:

$$\dot{C}_p = -(k_{10} + k_{12} + k_{13}) C_p + k_{21} C_{RD} + k_{31} C_{SD} \quad \text{(Equation 6)}$$

wherein
$k_{10}$ represents the elimination constant of a n applied drug, such as propofol from the body,
$k_{12}$ is an elimination constant describing the distribution of propofol from the central compartment A in direction of rapid equilibrating compartment $C_{RD}$,
$k_{21}$ is an elimination constant describing the distribution of propofol from rapid equilibrating compartment $C_{RD}$ in direction of central compartment A, $k_{13}$ is an elimination constant describing the distribution of propofol from central compartment A in direction of slow equilibrating compartment $C_{SD}$, $k_{31}$ is an elimination constant describing the distribution of propofol from slow equilibrating compartment $C_{SD}$ in direction of central compartment A, $C_{RD}$ represents a rapid equilibrating compartment;

$C_{SD}$ represents a slow equilibrating compartment; and $C_p$ represents the blood concentration.

Suitably, the model parameters $k_{e0}$ and $k_{1e}$ are tunable online during anesthesia. In particular, instant invention provides a method, wherein the model parameters $k_{e0}$ and $k_{1e}$ are tunable online according to the BIS value at the $EC_{50}$ and $EC_{95}$ points during anesthesia. Being tunable online means that the model parameters $\hat{k}_{1e}$ and $\hat{k}_{e0}$ are readjustable in order to have at the time of loss of consciousness the effect compartment concentration $C_e$ equal to the value $C_{e50}$ as set out in equation 7:

$$C_e(t_{LOC}, k_{e0}, k_{1e}) \equiv C_{e50} \quad \text{(Equation 7)}$$

wherein $C_e$ represents the effect compartment concentration;

$t_{LOC}$ represents the time point of loss of consciousness;

$k_{e0}$ defines the decay rate for the propofol effect;

$k_{1e}$ describes a "virtual" constant rate transfer from central compartment A and the effect compartment E; and $C_{e50}$ represents the effect compartment concentration at the $EC_{50}$ point according to equation 8:

$$C_{e50} = \frac{(E_0 - \text{Effect})^{\frac{1}{y}} \cdot EC_{50}}{(E_{max} - (E_0 - \text{Effect}))^{\frac{1}{y}}} \quad \text{(Equation 8)}$$

wherein Effect represents the concentration-effect relationship between $EC_{50}$ and the BIS index, wherein equation 8 is deduced form equation 9:

$$\text{Effect} = E_0 - \frac{E_{max} \cdot C_{e50}^y}{EC_{50}^y + C_{e50}^y} \quad \text{(Equation 9)}$$

wherein equation 10 is applicable:

$$C_e(t_{LOC}, \hat{k}_{e0}, \hat{k}_{1e}) \equiv C_{e50} \quad \text{(Equation 10)}$$

wherein in equations 8 to 10:

$E_0$ represents the initial value of the BIS effect at time point zero;

$E_{max}$ represents the maximum value of the BIS effect;

y represents the Hill coefficient, $EC_{50}$ defines how much propofol needs to be administered to obtain an effect in 50% of the patient population $t_{LOC}$ represents the time point of loss of consciousness;

$k_{e0}$ defines the proportional change in each unit of time of the concentration gradient between the plasma and effect-site $k_{1e}$ describes an elimination constant for redistribution of propofol from the effect compartment E to the central compartment A; and $C_{e50}$ represents the effect compartment concentration at the $EC_{50}$ point $EC_{50}$ concentrations shift when propofol is infused in combination with other substances, such as analgesics, like alfentanil or remifentanil. Accordingly, the control device and method of the invention can take into account interactions of propofol with other drugs, such as analgesics like Alfentanil® or Remifentanil®. This is accomplished by a recalibration of the extended 3+1 PK/PD model of the invention, after at least one analgesic has been administered.

The further advantage of the instant invention is that the compartments of the extended 3+1 PK/PD model are re-estimated in real-time. This is preferably accomplished by using a Luenberger observer. A Luenberger observer belongs to the state observers, which provide an estimate of the internal state of a given real system, from measurements of the input and output of the real system. State observers, such as a Luenberger observer, are known to the person skilled in the art.

The controller used in the control device and the method according to the invention may be a model-based controller, suitably a controller based on the extended 3+1 PK/PD model as described above. This has the advantage that BIS data can be taken into account to achieve a BIS target value rather than to achieve a concentration target value of propofol. The use of said model-based controller supports the control of the administration of propofol to a patient in real-time.

If a drug concentration measurement system (drug sensor) is available, the model compartments are re-estimated in real-time using a Luenberger observer. The controller is still a model-based controller to allow plug/unplug of the sensor at different instants of the surgery, where more accuracy is required.

The object of the invention is further achieved by a method for controlling the administration of propofol to a patient, in which:

a target BIS value is set, and a controller computes a recommended infusion rate for administering propofol to the patient based on the target BIS value and optionally the measured propofol level of a patient.

Herein, the method further comprises the determination of a propofol sensitivity of the patient by means of a mathematical model taking into account the bispectral index (BIS) and optionally the measured propofol level, and tuning of parameters of the mathematical model according to the depth of anesthesia and/or the level of the anesthetic in the body of said patient.

The advantages and advantageous embodiments described above with regard to the control device equally apply also to the method of the invention, such that it shall be referred to the above.

The idea underlying the invention shall subsequently be described in more detail with regard to the embodiments shown in the figures. Herein:

Figure 1:
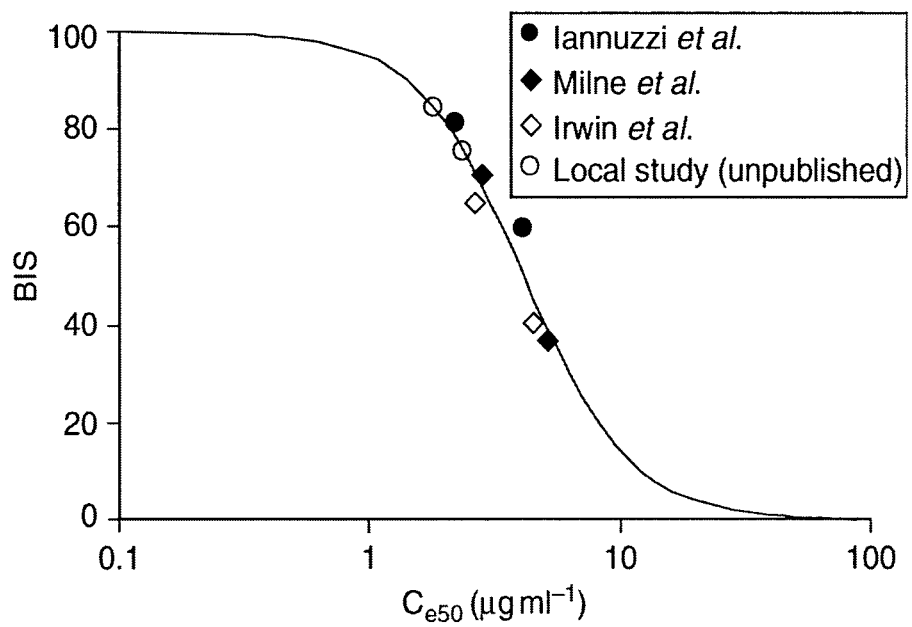
FIG. 1 shows the relationship between the propofol effective concentration 50 ($EC_{50}$) and the bispectral index (BIS)

FIG. 1 shows the relationship between the propofol effective concentration 50 ($EC_{50}$) and the bispectral index (BIS). FIG. 1 has been disclosed in the publication from T. A. Lim "Relationship between bispectral index and effect-site $EC_{50}$ for propofol" *Br J Anaesth*, 2006, 267-268, where corroborating results on different patient populations were reviewed and summarized. This information provides a way to relate the effect-site concentration and the bispectral index (BIS) at defined points, such as at loss of consciousness (LOC) or at the point of anesthesia.

The concentration-effect relationship between $EC_{50}$ and the BIS illustrated in FIG. 1 is derived by the equation according to Hill as follows:

$$\text{Effect} = E_0 - \frac{E_{max} \cdot C_{e50}{}^y}{EC_{50}{}^y + C_{e50}{}^y}$$

wherein $EC_{50}=4.14$ µg/ml for propofol, $E_{max}=E_0=100$ and $y=2$.

Figure 2:
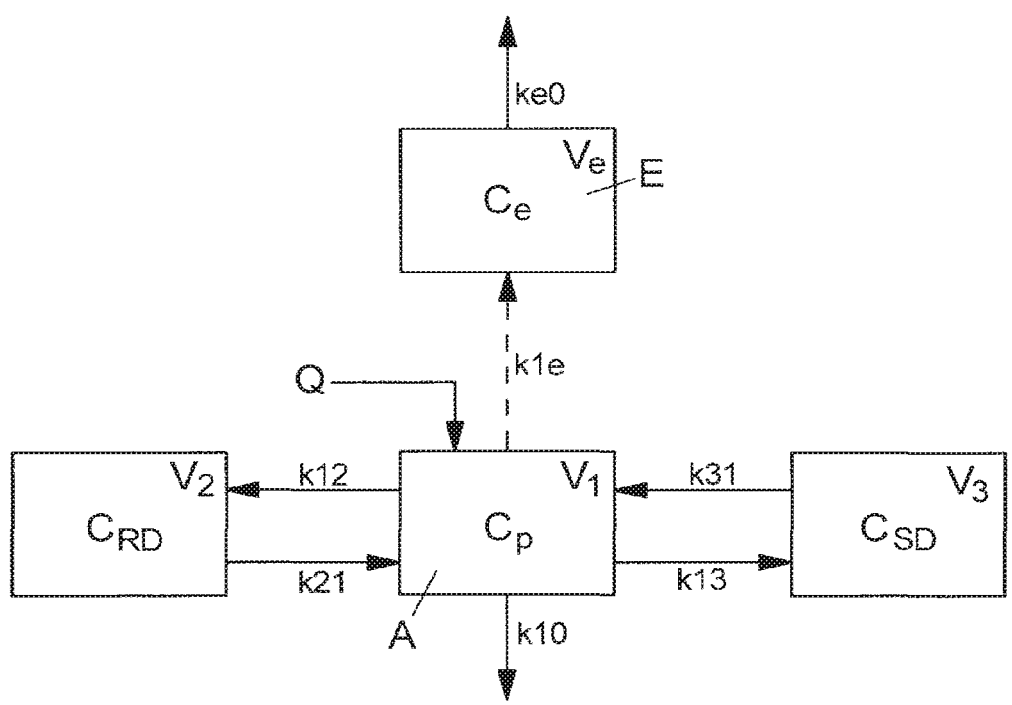
FIG. 2 shows a schematic diagram of the 3+1 PK/PD model as known in the prior art.

FIG. 2 shows a schematic diagram of the 3+1 PK/PD model as known in the prior art. Said 3+1 PK/PD model comprises a central compartment A comprising a blood concentration $C_p$ of propofol, a rapid equilibrating compartment $C_{RD}$, a slow equilibrating compartment $C_{SD}$, an effect compartment E comprising an effect compartment concentration $C_e$ of propofol.
wherein
Q represents an administered drug,
$k_{e0}$ defines the proportional change in each unit of time of the concentration gradient between the plasma and effect-site,
$k_{1e}$ describes an elimination constant for redistribution of propofol from the effect compartment E to the central compartment A,
$k_{12}$ is an elimination constant describing the distribution of the volume V1 in direction of volume V2,
$k_{21}$ is an elimination constant describing the distribution of the volume V2 in direction of volume V1,
$k_{13}$ is an elimination constant describing the distribution of the volume V1 in direction of volume V3,
$k_{31}$ is an elimination constant describing the distribution of the volume V3 in direction of volume V1,
$k_{10}$ represents the elimination constant of a n applied drug, such as propofol from the body.

FIG. 2 visualizes the so called Schnider model, which can be described as follows: After intravenous injection, a drug Q is rapidly distributed in the circulation (called the central compartment A) and quickly reaches well perfused tissues. Then, a tissue-specific redistribution in various other compartments such as muscle or fat tissue and vice versa from the central compartment A occurs. At the same time the body eliminates the applied substance from the central compartment with a certain elimination rate. For the pharmacokinetic characterization of lipophilic anesthetics, a 3-compartment model has been established that comprises a central compartment A (heart, lung, kidney, brain), a rapid equilibrating compartment $C_{RD}$ (muscles, inner organs), and a slow equilibrating compartment $C_{SD}$ (fat, bone, the so-called "deep" compartment). The concentration-time curve of a drug is characterized by the distribution volume of a specific compartment and the clearance (which is the plasma volume, from which the drug is eliminated per time unit): V1 is used as the volume of the central compartment A, V2 as the volume of the well-perfused tissue $C_{RD}$ and V3 as the volume of the rather worse perfused compartment $C_{SD}$. The clearance of a substance from the various compartments can be described by elimination constants and included by definition, a description of the distribution direction: The elimination constant $k_{12}$ for example, describes the distribution of the volume V1 in direction V2, $k_{21}$ describes the distribution in the opposite direction. An applied substance is eliminated by this model with the constant $k_{10}$ from the body. After reaching an equilibrium ("Steady state") between the individual compartments, the elimination rate determines the amount of substance that must be supplied to maintain equilibrium. An intravenously administered anesthetic is first distributed within the central compartment A. From there, the distribution will take place into the effect compartment E and into the peripheral compartments. The substance is eliminated by the constant $k_{10}$ from the central compartment A.

To assess the clinical effect (the so-called pharmacodynamics) of a drug at the target site, dose-response curves are used. These usually sigmoidal extending curves describe the association between drug concentration and the particular clinical effect. Knowing these dose-response relationship, a putative drug concentration at the site of action, the effect compartment E, can be calculated. The delay between the maximum plasma concentration and the maximum clinical effect is called hysteresis.

Figure 3:
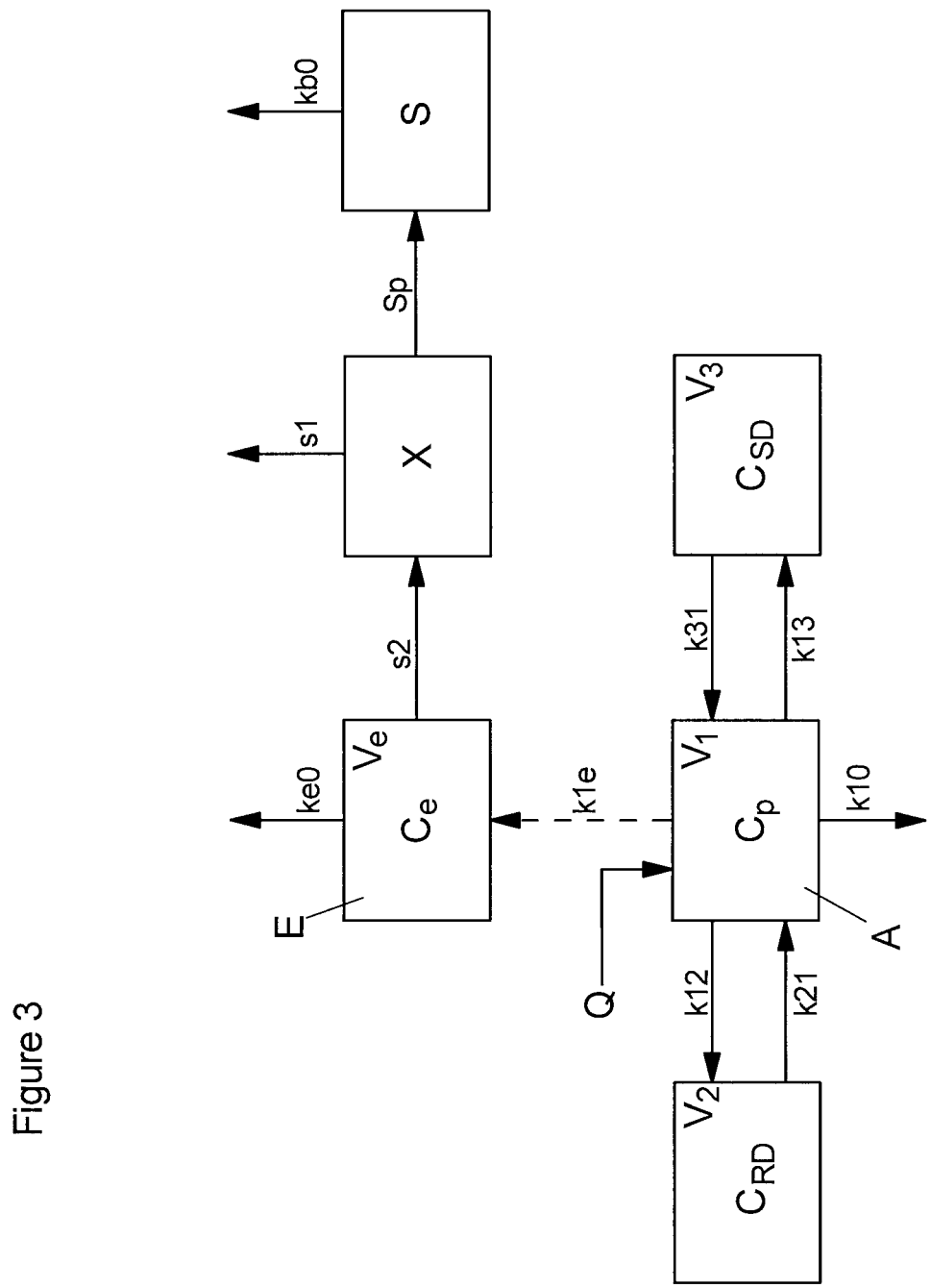
FIG. 3 shows a schematic diagram of the extended 3+1 PK/PD model of the instant invention.

FIG. 3 shows a schematic diagram of the extended 3+1 PK/PD model of the instant invention, which additionally comprises a remote compartment X and a BIS sensor S, wherein
s1 and s2 represent constant transfer rate parameters between the remote compartment X and the effect compartment E,
$S_P$ represents a transfer rate coefficient between the remote compartment X and the depth-of-anesthesia monitor S, and
$k_{b0}$ represents the decay rate of the BIS index.

Clinically, $S_P$ can be seen as the propofol sensitivity. The higher the value of $S_P$ is, the faster is the propofol effect achieved. High values of $S_P$ further lead to a short delay of the system and a high responsiveness of the system.

The remote compartment X describes the delay between the propofol concentration in the effect-site compartment and its actual impact on the BIS value.

The compartment S represents a patient-dependent BIS sensor, i.e. the actual BIS value displayed on the monitor.

Figure 4:
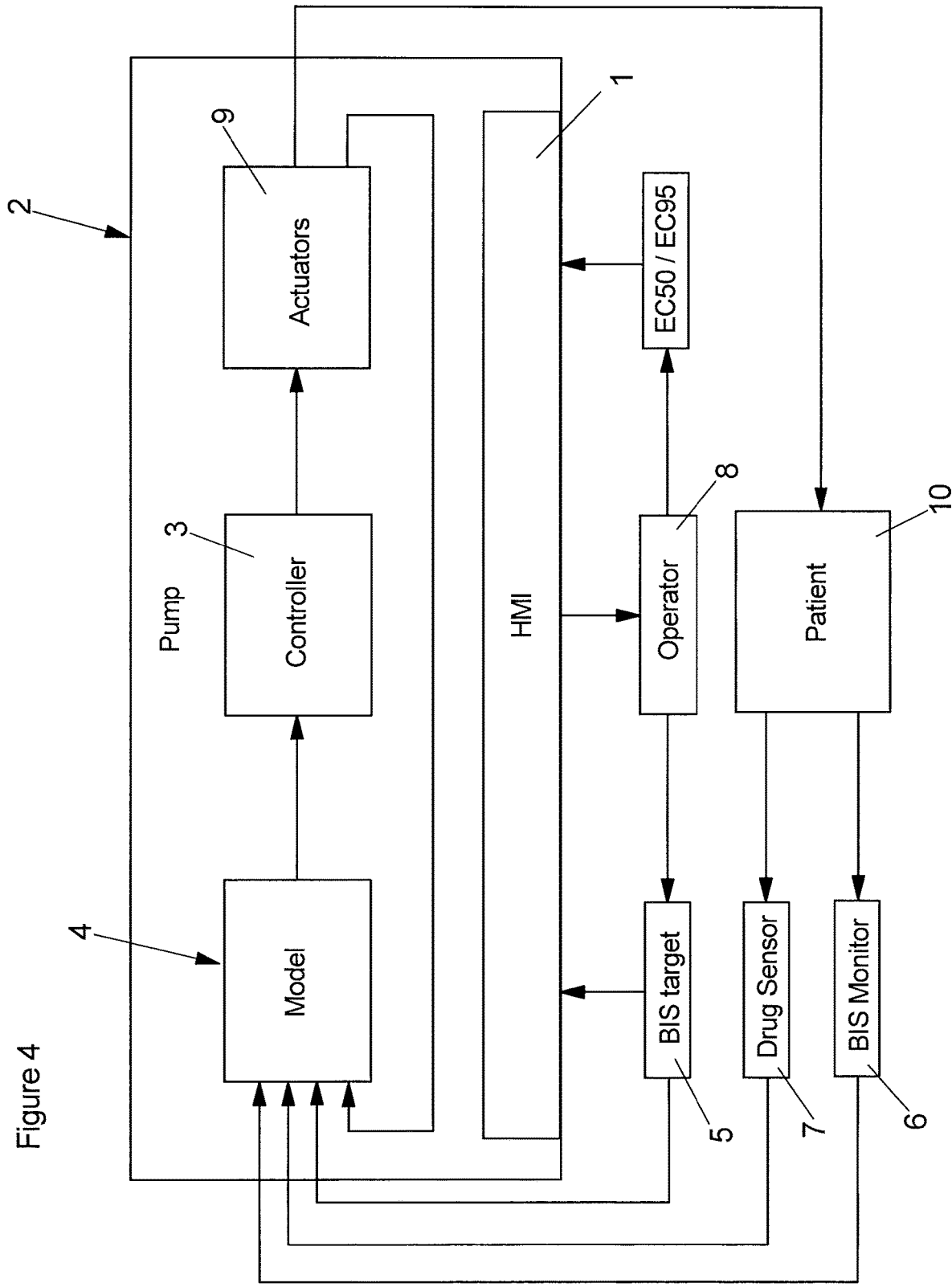
FIG. 4 shows a schematic diagram of the control device.

FIG. 4 shows a schematic diagram of the control device for controlling the administration of propofol to a patient comprising a human machine interface (1), an infusion pump (2) which comprises a controller (3) for computing a infusion rate for administering propofol to the patient, a depth-of-anesthesia monitor (6), such as a bispectral index (BIS) monitor, and optionally a drug sensor (7), which further comprises, in accordance with the invention, a target setting unit (5) for setting a BIS target value and a model unit (4) for determining the propofol sensitivity of a patient by means of a mathematical model taking into account the bispectral index (BIS) and optionally the measured propofol level. The control device may further comprise at least one actuator. Actuators in the sense of the present invention are any mechanical parts of the infusion pump, including for example a motor or other mechanical parts between the model-driven controller and the injection syringe.

Typically, when using the control device according to the invention, the operator first plugs on the depth-of-anesthesia monitor (6), such as a BIS monitor. The operator is typically an anesthetist or an anesthesia nurse. Thereafter, a model for target controlled infusion (TCI) for propofol is chosen and set in the control device.

TCI models for propofol are known in the art. The recently introduced open-target-controlled infusion (TCI) systems can be programmed with any pharmacokinetic model, and allow either plasma- or effect-site targeting. With effect-site targeting the goal is to achieve a user-defined target effect-site concentration as rapidly as possible, by manipulating the plasma concentration around the target. Currently systems are pre-programmed with the Marsh (B. Marsh et al., "Pharmacokinetic model driven infusion of propofol in children" *Br J Anaesth,* 1991; 67, pages 41-48) and Schnider (Thomas W. Schnider et al., "The influence of method of administration and covariates on the pharmacokinetics of propofol in adult volunteers", *Anesthesiology,* 1998, 88(5) pages 1170-82) pharmacokinetic models for propofol. The former is an adapted version of the Gepts model, in which the rate constants are fixed, whereas compartment volumes and clearances are weighed proportional. The Schnider model was developed during combined pharmacokinetic-pharmacodynamic modelling studies. It has fixed values for certain parameters, such as $k_{13}$, and $k_{31}$, adjusts others, $k_{12}$, and $k_{21}$ for age, and adjusts $k_{10}$ according to total weight, lean body mass (LBM), and height. In plasma targeting mode, the Schnider model starts with smaller initial doses on starting the system or on increasing the target concentration in comparison with the Marsh model. The Schnider model should thus always be used in effect-site targeting mode, in which larger initial doses are administered, albeit still smaller than for the Marsh model.

Having chosen the appropriate TCI model, the operator (8) has then to enter patient parameters, such as age, gender, total weight, lean body mass (LBM) and height, for example. After the synchronization of the model/BIS in order to tune the OFFSET parameter of the model has occurred, the BIS target value (5) has to be set by the operator (8). It can further be chosen whether the control device works in ramp mode or not, wherein ramp mode has been demonstrated as best practice to increase the patient's sensitivity to propofol. Ramp mode means that a desired BIS target value is not reached in a direct, linear manner, but in a stepwise manner. In contrast, if ramp mode is not chosen, a time for achievement a BIS target value is to be set, representing the aggressiveness of the controller. In the next step, the protocol is started. At the point of loss of consciousness (LOC), the operator typically will click on the LOC button on the system (infusion pump or machine). This will give a feedback to the protocol that the $EC_{50}$ has been reached and will recalibrate the model according to the patient parameters and the actual BIS value. To further improve precision, the physician optionally informs the system at the $EC_{95}$ value. Several techniques exist to determine this value easily during the surgery, e.g. just before starting surgery.

Figure 5:
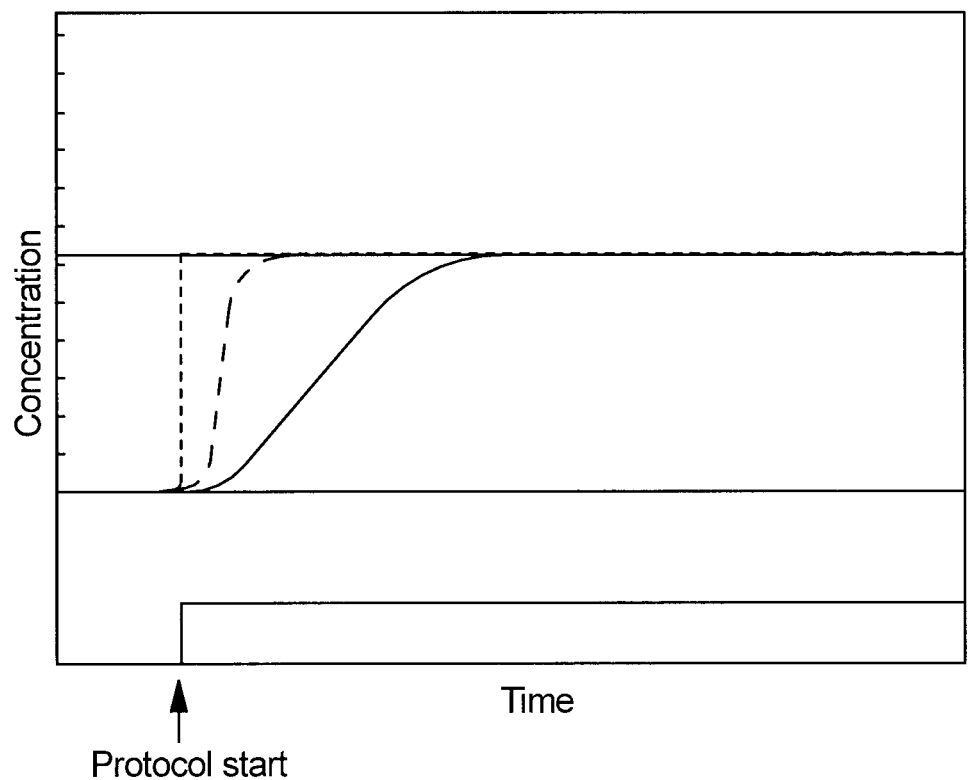
FIG. 5 shows a concentration-time diagram, displaying different aggressiveness of the controller.

FIG. 5 shows a concentration-time diagram, displaying different aggressiveness of the controller. As described for FIG. 4, the operator sets a BIS target value to the infusion pump and the controller uses the PK/PD model to compute the correct infusion rate to administer propofol to the patient to achieve the BIS target value. The controller of the invention (optionally in combination with PID controller with Smith predictor) is capable of avoiding overdosing of propofol when using a system with high delay. The controller can predict different scenarios in the future using trajectory generation and tracking to achieve the desired BIS target value. This technique further enables the operator to choose the time of target achievement, i.e. to choose the "aggressiveness" of the controller. FIG. 5 shows exemplary different "aggressiveness" trajectories of the controller. Short-dashed line, semi-dashed line and plain line represents high, medium and low aggressiveness, respectively.

Accordingly, the invention further provides a method of using of the control device according to invention, comprising the steps of:

a) plugging the depth-of-anesthesia monitor (6), b) choosing a TCI model and entering patient parameters, c) waiting for TCI model/BIS synchronization, d) setting the BIS index target (5), e) selecting ramp mode or not, f) starting the protocol, g) at loss of consciousness point, clicking on the LOC button on the infusion device, such as the infusion pump or the infusion machine, h) optionally, informing the control device at the $EC_{95}$; and i) further optionally choosing the time of target achievement (aggressiveness of the controller).

The idea of the invention is not limited to the embodiments described above.

In particular, the system described above in principal may also be set up as a closed-loop system which does not require interaction by an operator. For this, an infusion rate may automatically be sent by the controller to the infusion pump for administration of propofol to the patient, and a propofol level measurement may be taken automatically, for example in a periodic fashion at predefined measurement times for providing a feedback to the control device.

LIST OF REFERENCE NUMERALS

1 Human machine interface
2 Infusion pump
3 Controller
4 Model unit
5 BIS Target value
6 BIS Monitor
7 Drug Sensor
8 Operator
9 Actuator
10 Patient
A Central compartment
E Effect compartment
Q Administered drug infusion rate

The invention claimed is:

1. A control device for controlling the administration of propofol to a patient comprising
a human machine interface,
an infusion pump which comprises a controller for computing a recommended infusion rate for administering propofol to the patient,
a depth-of-anesthesia monitor,
a target setting unit for setting a BIS target, and
a model unit for determining the propofol sensitivity of a patient by means of a mathematical model taking into account the bispectral index (BIS), wherein the mathematical model is based on a PK/PD model which comprises a 3+1 PK/PD model, a remote compartment X and a compartment S;
wherein the compartment S represents the bisprectral index (BIS) and is represented by the following equation:

$$S = \frac{s_p X}{\alpha_M + X} - k_{b0} S + OF$$

wherein
$s_P$ represents the propofol sensitivity of the patient;
$\alpha_M$ represents the saturation parameters of the velocity of effect of an anesthetic;
$k_{b0}$ represents the decay rate of the BIS index;

OF represents the offset that can remain when no more anesthetic is present in the patient body;

X represents a remote compartment; and

S represents a BIS sensor and the remote compartment X models the delay between the propofol concentration in the effect site compartment and its actual impact on the bispectral index (BIS).

2. The control device according to claim 1, wherein the infusion pump further comprises at least one actuator.

3. The control device according to claim 1, wherein said control device is based on a closed-loop system, wherein an infusion rate of propofol is sent automatically by the controller to the infusion pump for administering propofol to the patient.

4. The control device according to claim 1, wherein the 3+1 PK/PD model is based on a central compartment A comprising a blood concentration $C_p$ of propofol, a rapid equilibrating compartment $C_{RD}$, a slow equilibrating compartment $C_{SD}$, an effect compartment E comprising an effect compartment concentration $C_e$ of propofol.

5. The control device according to claim 1 further comprising a drug sensor, and the mathematical model taking into account the measured propofol level.

6. The control device according to claim 1 wherein a propofol level measurement is performed automatically and periodically at predefined measurement times for providing a feedback to the controller.

7. The control device according to claim 1, further comprising a drug sensor.

8. The control device according to claim 7, wherein the compartments of the PK/PD model are re-estimated in real-time.

9. The control device according to claim 7, wherein the controller is a model-based controller.

10. The control device according to claim 7, wherein the controller allows the plugging and unplugging of the drug sensor.

11. The control device according to claim 7, wherein the compartments of the PK/PD model are re-estimated in real-time using a Luenberger observer.

12. The control device according to claim 1, wherein $\hat{k}_{1e}$ and $\hat{k}_{e0}$ are model parameters that are defined below and readjusted in order to have, at the time of loss of consciousness, the effect compartment concentration $C_e$ equal to the value $C_{e50}$ as set out in a first equation:

$$C_e(t_{LOC}, \hat{k}_{e0}, \hat{k}_{1e}) = C_{e50}$$

wherein $C_e$ represents the effect compartment concentration;

$t_{LOC}$ represents the time point of loss of consciousness;

$k_{e0}$ defines the proportional change in each unit of time of the concentration gradient between the plasma and effect-site, $k_{1e}$ describes an elimination constant for redistribution of propofol from the effect compartment E to the central compartment A; and wherein $C_{e50}$ represents the effect compartment concentration at the $EC_{50}$ point according to a second equation:

$$C_{e50} = \frac{(E_0 - \text{Effect})^{\frac{1}{y}} \cdot EC_{50}}{(E_{max} - (E_0 - \text{Effect}))^{\frac{1}{y}}}$$

wherein Effect represents the concentration-effect relationship between $EC_{50}$ and the BIS index, wherein the second equation is deduced from a third equation:

$$\text{Effect} = E_0 - \frac{E_{max} \cdot C_{e50}{}^y}{EC_{50}{}^y + C_{e50}{}^y}$$

wherein in the second equation and the third equation:

$E_0$ represents the initial value of the BIS effect at time point zero;

$E_{max}$ represents the maximum value of the BIS effect;

y represents the Hill coefficient;

$EC_{50}$ defines how much drug needs to be administered to obtain an effect in 50% of the patient population.

13. The control device according to claim 12, wherein said control device takes into account interactions of propofol with other drugs comprising analgesics, said analgesics including Alfentanil and Remifentanil.

14. The control device according to claim 13, wherein the PK/PD model is recalibrated, after at least one analgesic has been administered.

15. The control device according to claim 1, wherein the delay which the remote compartment X models between the propofol concentration in the effect site compartment and its actual impact on the bispectral index (BIS), comprises physiological delay, and computational delay induced by signal processing in the bispectral index (BIS).

16. The control device according to claim 15 wherein remote compartment X is represented by the following equation:

$$\dot{X} = s_2 C_e - s_1 X$$

wherein $s_1$ and $s_2$ represent constant transfer rate parameters between the remote compartment X and the effect compartment E;

$C_e$ represents the effect compartment concentration; and

X represents a remote compartment.

17. A method for controlling the administration of propofol to a patient, comprising the steps of:

setting a target BIS value on a BIS sensor, and setting a controller to compute a recommended infusion rate for administering propofol to the patient based on the target BIS value, estimating a propofol sensitivity of the patient with the use of a mathematical model taking into account the bispectral index (BIS) wherein the mathematic model is based on a PK/PD model comprising a 3+1 PK/PD model, a compartment S representing a BIS sensor and is represented by the following equation:

$$S = \frac{s_p X}{\alpha_M + X} - k_{b0} S + OF$$

wherein $s_p$ represents the propofol sensitivity of the patient;

$\alpha_M$ represents the saturation parameters of the velocity of effect of an anesthetic;

$k_{b0}$ represents the decay rate of the BIS index;

OF represents the offset that can remain when no more anesthetic is present in the patient body;

X represents a remote compartment; and

S represents a BIS sensor, and a remote compartment X modeling the delay between the propofol concentration in the effect site compartment and the actual impact on the BIS sensor, and tuning parameters of the mathematical model according to the depth of anesthesia and/or the level of the anesthetic in the body of said patient.

18. The method according to claim 17 wherein the controller computes a recommended infusion rate for administering propofol to the patient based on the measured propofol level of the patient.

19. The method according to claim 17, wherein the 3+1 PK/PD model is based on a central compartment A comprising a blood concentration $C_p$ of propofol, a rapid equilibrating compartment $C_{RD}$, a slow equilibrating compartment $C_{SD}$, an effect compartment E comprising an effect compartment concentration $C_e$ of propofol.

* * * * *